US006225530B1

(12) United States Patent
Weigel et al.

(10) Patent No.: US 6,225,530 B1
(45) Date of Patent: May 1, 2001

(54) FLOWERING LOCUS T (FT) AND GENETICALLY MODIFIED PLANTS HAVING MODULATED FLOWER DEVELOPMENT

(75) Inventors: Detlef Weigel, Solana Beach; Igor Kardailsky, Albany, both of CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/060,726

(22) Filed: Apr. 15, 1998

(51) Int. Cl.[7] .................. C12N 15/29; C12N 15/82; C12N 15/84; A01H 5/00; A01H 5/10

(52) U.S. Cl. ............... 800/290; 435/69.1; 435/320.1; 435/419; 435/468; 435/469; 435/471; 536/23.6; 800/294; 800/298

(58) Field of Search .................. 435/69.1, 320.1, 435/410, 419, 468, 471, 469; 536/23.6, 24.1; 800/278, 290, 294, 295, 298

(56) References Cited

FOREIGN PATENT DOCUMENTS

WO 97/10339   3/1997 (WO) .............. C12N/15/29
WO 97/46077 * 12/1997 (WO) .............. A01H/5/00

OTHER PUBLICATIONS

Ruiz–Garia et al, Plant Cell, vol. 9, pp. 1921–1934, 1997.*
Vysotskaia, et al. (Direct Submission, Accession No. 004467), see alignment. 1 pp.
Bradley, et al. (Direct Submission, Accession No. W13945), see alignment, 2 pp.

* cited by examiner

Primary Examiner—Gary Benzion
Assistant Examiner—Ashwin D. Mehta
(74) Attorney, Agent, or Firm—Knobbe, Martens, Olson & Bear LLP

(57) ABSTRACT

The present invention provides a gene, termed "FT" for flowering locus T, and a polypeptide encoded by FT that modulates flower development in plants. FT is useful in methods of the invention for producing genetically modified plants characterized as having the phenotypic trait of modulated flower development, for example early or delayed flowering. Such plants can be genetically modified by nucleic acids encoding functional FT peptides; at least one antisense nucleic acid for FT; a structural gene that encodes wild-type FT polypeptide; or a structural gene that encodes dominant negative polypeptides, for example, in order to modulate flowering in the plant.

41 Claims, 4 Drawing Sheets

FT sense insert (814 bp without vector sequences)

Xba I
TCTAGAACTAGTGGATCCCCCGGGCTCCAGGAATTCAGCACGAGGTTTGTTCAAGATCAAAG

ATGTCTATAAATATAAGAGACCCTCTTATAGTAAGCAGAGTTGTTGGAGACGTTCTTGAT
MetSerIleAsnIleArgAspProLeuIleValSerArgValValGlyAspValLeuAsp

CCGTTTAATAGATCAATCACTCTAAAGGTTACTTATGGCCAAAGAGAGGTGACTAATGGC
ProPheAsnArgSerIleThrLeuLysValThrTyrGlyGlnArgGluValThrAsnGly

TTGGATCTAAGGCCTTCTCAGGTTCAAAACAAGCCAAGAGTTGAGATTGGTGGAGAAGAC
LeuAspLeuArgProSerGlnValGlnAsnLysProArgValGluIleGlyGlyGluAsp

CTCAGGAACTTCTATACTTTGGTTATGGTGGATCCAGATGTTCCAAGTCCTAGCAACCCT
LeuArgAsnPheTyrThrLeuValMetValAspProAspValProSerProSerAsnPro

CACCTCCGAGAATATCTCCATTGGTTGGTGACTGATATCCCTGCTACAACTGGAACAACC
HisLeuArgGluTyrLeuHisTrpLeuValThrAspIleProAlaThrThrGlyThrThr

TTTGGCAATGAGATTGTGTGTTACGAAAATCCAAGTCCCACTGCAGGAATTCATCGTGTC
PheGlyAsnGluIleValCysTyrGluAsnProSerProThrAlaGlyIleHisArgVal

GTGTTTATATTGTTTCGACAGCTTGGCAGGCAAACAGTGTATGCACCAGGGTGGCGCCAG
ValPheIleLeuPheArgGlnLeuGlyArgGlnThrValTyrAlaProGlyTrpArgGln

AACTTCAACACTCGCGAGTTTGCTGAGATCTACAATCTCGGCCTTCCCGTGGCCGCAGTT
AsnPheAsnThrArgGluPheAlaGluIleTyrAsnLeuGlyLeuProValAlaAlaVal

TTCTACAATTGTCAGAGGGAGAGTGGCTGCGGAGGAAGAAGACTTTAGATGGCTTCTTCC
PheTyrAsnCysGlnArgGluSerGlyCysGlyGlyArgArgLeu***

TTTATAACCAATTGATATTGCATACTCTGATGAGATTTATGCATCTATAGTATTTTAATT
TAATAACCATTTTATGATACGAGTAACGAACGGTGATGATGCCTATAGTAGTTCAATATA
TAAGTGTGTAATAAAAATGAGAGGGGGAGGAAAATGAGAGTGTTTTACTTATATAGTGTG
TGATGCGATAATTATATTAATCTACATGAAATGAAGTGTTATATTTATAAAAAAAAAAAA

Xho I
AAAAAAAACTCGAG

FT antisense sense insert (814 bp without vector sequences)

CTCGAGTTTTTTTTTTTTTTTTTTATAAATATAACACTTCATTTCATGTAGATTAATA
TAATTATCGCATCACACACTATATAAGTAAAACACTCTCATTTTCCTCCCCCTCTCATTT
TTATTACACACTTATATATTGAACTACTATAGGCATCATCACCGTTCGTTACTCGTATCA
TAAAATGGTTATTAAATTAAAATACTATAGATGCATAAATCTCATCAGAGTATGCAATAT
CAATTGGTTATAAAGGAAGAAGCCATCTAAAGTCTTCTTCCTCCGCAGCCACTCTCCCTC
TGACAATTGTAGAAAACTGCGGCCACGGGAAGGCCGAGATTGTAGATCTCAGCAAACTCG
CGAGTGTTGAAGTTCTGGCGCCACCCTGGTGCATACACTGTTTGCCTGCCAAGCTGTCGA
ACAATATAAACACGACACGATGAATTCCTGCAGTGGGACTTGGATTTTCGTAACACACA
ATCTCATTGCCAAAGGTTGTTCCAGTTGTAGCAGGGATATCAGTCACCAACCAATGGAGA
TATTCTCGGAGGTGAGGGTTGCTAGGACTTGGAACATCTGGATCCACCATAACCAAAGTA
TAGAAGTTCCTGAGGTCTTCTCCACCAATCTCAACTCTTGGCTTGTTTTGAACCTGAGAA
GGCCTTAGATCCAAGCCATTAGTCACCTCTCTTTGGCCATAAGTAACCTTTAGAGTGATT
GATCTATTAAACGGATCAAGAACGTCTCCAACAACTCTGCTTACTATAAGAGGGTCTCTT
ATATTTATAGACATCTTTGATCTTGAACAAACCTCGTGCTGAATTCCTGCAGCCCGGGGG

Xba I
ATCCACTAGTTCTAGA

```
1   M-- ...... DPLIV.RVVGDVLD.F .... L.V.YG .. VTN-G .. L.PSQV.NKPR-VEI.G.DLR        At FT
1   M ......... PLI.GRVVGDVLD.F.PT ... V.Y .. K.V.N-G.EL.PS.V .. KPR-VEI.G.DLR        At TFL1
1   MAA-- --.. DPLI.GRVVGDVLD.F.PT ... V.Y .. K.V.N-G.EL.PS.V .. KPR-VEI.G.DLR        At E12A11
1   MAA ....... PL.... V ..------ P ... L.V.YG .. V ... G .. L.P.QV.N.P ...... G.D..   Rn HCNP

63  .. YTLVM.DPD.PSPS.P.LRE.LHWLV.DIP.TT ... FG.EIV.YE.P.P .--. GIHR.VF.LFRQ          At FT
66  ... TLVM.DPD.P.PSDP.L.E.LHW.V .. IPGTTD .. FGKE.V.YE.PRP .--. GIHR.VFVLFRQ        At TFL1
61  .LYTLVMTDPPDAPSPS.P .. REW.HW.VVDIPG.T..S.GKEI..Y..PRPP--.GIHRY..VLFRQ           At E12A11
62  .LYTLV.TDPDAPS .. DP .. REW H.LVV ... G.-D.S.G .... Y .... PP ... G.HRYV ..... Q  Rn HCNP

128 ..R------ ........ -G-..R.NFNTR.FA..Y.LGLPVAAVF.N.QRE .... RR------.             At FT
131 ..QR------ ....... G.SR..FNTR.FA..YDLGLGLPVAAVF.NAQRE.--A.RR------R.             At TFL1
126 ..-------L ...... G.SR.NF.TR.FA... DLGLPVA.VF.NAQRE.--A.RR------R.               At E12A11
128 ..Q--------- ..... G...R..F .... F....Y.LG.PVA...F AQRE .........                Rn HCNP
```

FIGURE 3C

```
S I N I - - R D P L    At FT
E N M G T R V I E P L  At TFL1
A A K V S - - S D P L  Am CEN
A A S - - - V D P L    At E12A11
A A D I S Q W A G P L  Rn HCNP
P V D L S K W S G P L  Hs HCNP
```

FLOWERING LOCUS T (FT) AND GENETICALLY MODIFIED PLANTS HAVING MODULATED FLOWER DEVELOPMENT

TECHNICAL FIELD

This invention relates generally to plant genetic engineering, and specifically to novel genetically engineered plants characterized as having a phenotype of modulated flower development and methods for producing such plants.

BACKGROUND

Most angiosperm species are induced to flower in response to environmental stimuli such as day length and temperature, and internal cues, such as age. Adult organs of flowering plants develop from groups of stem cells called meristems. The identity of a meristem is inferred from structures it produces: vegetative meristems give rise to roots and leaves, inflorescence meristems give rise to flower meristems, and flower meristems give rise to floral organs such as sepals and petals. Not only are meristems capable of generating new meristems of different identity, but their own identity can change during development. For example, a vegetative shoot meristem can be transformed into an inflorescence meristem upon floral induction, and in some species, the inflorescence meristem itself will eventually become a flower meristem. Despite the importance of meristem transitions in plant development, little is known about the underlying mechanisms.

Following germination, the shoot meristem produces a series of leaf meristems on its flanks. However, once floral induction has occurred, the shoot meristem switches to the production of flower meristems. Flower meristems produce floral organ primordia, which develop individually into sepals, petals, stamens or carpels. Thus, flower formation can be thought of as a series of distinct developmental steps, i.e. floral induction, the formation of flower primordia and the production of flower organs. Mutations disrupting each of the steps have been isolated in a variety of species, suggesting that a genetic hierarchy directs the flowering process (see for review, Weigel and Meyerowitz, In *Molecular Basis of Morphogenesis* (ed. M. Bernfield). 51st Annual Symposium of the Society for Developmental Biology, pp. 93–107, New York, 1993).

Recently, studies of two distantly related dicotyledons, *Arabidopsis thaliana* and *Antirrhinum majus,* led to the identification of three classes of homeotic genes, acting alone or in combination to determine floral organ identity (Bowman, et al., *Development,* 112:1, 1991; Carpenter and Coen, *Genes Devl.,* 4:1483, 1990; Schwarz-Sommer, et al., *Science,* 250:931, 1990). Several of these genes are transcription factors whose conserved DNA-binding domain has been designated the MADS box (Schwarz-Sommer, et al., supra).

Earlier acting genes that control the identity of flower meristems have also been characterized. Flower meristems are derived from inflorescence meristems in both Arabidopsis and Antirrhinum. Two factors that control the development of meristematic cells into flowers are known. In Arabidopsis, the factors are the products of the LEAFY gene (Weigel, et al., *Cell* 69:843, 1992) and the APETALA1 gene (Mandel, et al., *Nature* 360:273, 1992). When either of these genes is inactivated by mutation, structures combining the properties of flowers and inflorescence develop (Weigel, et al., supra; Irish and Sussex, *Plant Cell,* 2:741, 1990). In Antirrhinum, the homologue of the Arabidopsis LEAFY gene is FLORICAULA (Coen, et al., *Cell,* 63:1311, 1990) and that of the APETALA1 gene is SQUAMOSA (Huijser, et al., *EMBO J.,* 11:1239, 1992). The latter pair contains MADS box domains.

Flowering plants exhibit one of two types of inflorescence architecture: indeterminate, in which the inflorescence grows indefinitely, or determinate, in which a terminal flower is produced. In two mutants in distantly related species, *terminal flower* 1 in Arabidopsis and *centroradialis* in Antirrhinum, inflorescences that are normally indeterminate are converted to a determinate architecture. The Antirrhinum gene CENTRORADIALIS (CEN) and the Arabidopsis gene TERMINAL FLOWER 1 (TFL1) were shown to be homologous, which suggests that a common mechanism underlies indeterminacy in these plants. However, unlike CEN, TFL1 is also expressed during the vegetative phase, where it delays the commitment to inflorescence development and thus affects the timing of the formation of the inflorescence meristem as well as its identity.

There is increasing incentive by those working in the field of plant biotechnology to successfully genetically engineer plants, including the major crop varieties. One genetic modification that would be economically desirable would be to accelerate the flowering time of a plant. Induction of flowering is often the limiting factor for growing crop plants. One of the most important factors controlling induction of flowering is day length, which varies seasonally as well as geographically. There is a need to develop a method for controlling and inducing flowering in plants, regardless of the locale or the environmental conditions, thereby allowing production of crops, at any given time. Since most crop products (e.g. seeds, grains, fruits), are derived from flowers, such a method for controlling flowering would be economically invaluable.

SUMMARY

The present invention is based on the discovery of a gene that regulates flowering in plants. The gene is termed "flowering locus T" or "FT" and functions to modulate flowering time. Overexpression of FT results in dramatic early flowering in Arabidopsis while loss of function mutations in FT or antisense directed to FT causes late flowering.

In a first embodiment, the invention provides FT polypeptide, which is characterized as having a molecular weight of approximately 20 kD, as determined by SDS-PAGE; being located on chromosome 1 of Arabidopsis; and functioning to modulate flowering time. An exemplary amino acid sequence of FT polypeptide is shown in SEQ ID NO:2. An exemplary FT peptide having flowering promoting activity is shown in SEQ ID NO:4 and more specifically in SEQ ID NO:6. Also included in the invention is an isolated polynucleotide that encodes FT polypeptide. An exemplary nucleotide sequence encoding FT is shown in SEQ ID NO:1 from nucleotide base 37 to 849.

In another embodiment, the invention provides a genetically modified plant including at least one exogenous nucleic acid sequence such as at least FT-encoding nucleic acid sequence in its genome and characterized as having modulated flower development. Flower development can be inhibited or accelerated by the method of the invention.

In another embodiment, the invention provides a method for genetically modifying a plant cell such that a plant, produced from the cell, is characterized as having modulated flower development as compared with a wild-type plant. The method includes introducing at least FT encoding polynucleotide of the invention into a plant cell to obtain a transformed plant cell; and growing the transformed plant cell under conditions which permit expression of FT polypeptide, thereby producing a plant having modulated flower development.

In yet another embodiment, the invention provides a method of producing a genetically modified plant characterized as having early flower development. The method includes contacting a plant cell with a vector containing a nucleic acid sequence comprising at least a structural gene encoding FT polypeptide, the gene operably associated with a promoter, to obtain a transformed plant cell; producing a plant from the transformed plant cells; and selecting a plant exhibiting early flower development.

In yet another embodiment, the invention provides a method for modulating flower development in a plant cell. The method includes contacting the plant cell with a vector containing a nucleic acid sequence having at least one structural gene encoding FT polypeptide to modulate flower development, operably associated with a promoter to obtain a transformed plant cell; growing the transformed plant cell under plant forming conditions; and inducing early flower development in the plant under conditions and for a time sufficient to modulate flower development. Modulation of flower development includes acceleration or inhibition of development.

The invention also provides a genetically modified plant having a transgene disrupting or interfering with, expression of flowering time gene (FT), chromosomally integrated into the genome of the plant. The invention also includes a method for producing such plants, characterized as having late flower development. The method includes contacting a plant cell with a vector containing a nucleic acid sequence including at least a structural gene disrupting or interfering with expression of FT polypeptide, wherein the gene is operably associated with a promoter, to obtain a transformed plant cell; producing a plant from the transformed plant cells; and selecting a plant exhibiting late flower development. The method also includes substituting the structural gene disrupting or interfering with expression of FT polypeptide with a vector containing an FT antisense nucleic acid sequence or FT dominant-negative encoding nucleic acid sequence.

In another embodiment, the invention provides a method for identifying a compound which modulates FT activity or gene expression. The method includes incubating components including the compound and FT polypeptide or a recombinant cell expressing FT, under conditions sufficient to allow the components to interact; and determining the effect of the compound on the activity or expression of FT. A compound may inhibit or may stimulate the activity or expression of FT.

In another embodiment, the invention provides a method for identifying a peptide of FT that either mimics or inhibits the activity or expression of wild-type FT. Such peptide can be used in place of wild-type FT, wherein wild-type FT is a control, in order to determine the effect on flowering time for the peptide.

DESCRIPTION OF DRAWINGS

FIG. 2 shows nucleotide sequences of FT cDNA inserts used for the sense and antisense constructs (pSKI059 (SEQ ID NO:1) and pSKI060 (SEQ ID NO:3). For the sense strand the conceptual translation of the FT protein is shown in three-letter code under the DNA sequence. Vector sequences are underlined.

At—*Arabidopsis thaliana;* Am—*Antirrhinum majus* (snapdragon); Rn—*Rattus norvegicus* (rat); Hs—*Homo sapiens.* TFL1—TERMINAL FLOWER 1 (Bradley et al., (1997), *Science* 275, 80–83); CEN—CENTRORADIALIS (Bradley et al., (1996), *Nature* 379, 791–797); E12A11—EST clone (partial sequence in GenBank [accession number AA042630]; complete sequence determined by Kardailsky & Weigel, unpublished); HCNP—hippocampal cholinergic neurostimulating peptide precursor protein (Ojika et al., (1992), *Brain Res.* 572, 164–171.(1992), *Brain Res.* 572, 164–171); Tohdoh et al., (1995), *Brain Res. Mol. Brain. Res.* 30, 381–384).

FIG. 3A shows the aligned amino acid sequences of entire proteins. Only amino acids present in at least two of the four aligned proteins are shown. Amino acids that differ from the consensus are indicated by dots, and gaps by horizontal dashes.

Figure 3B:
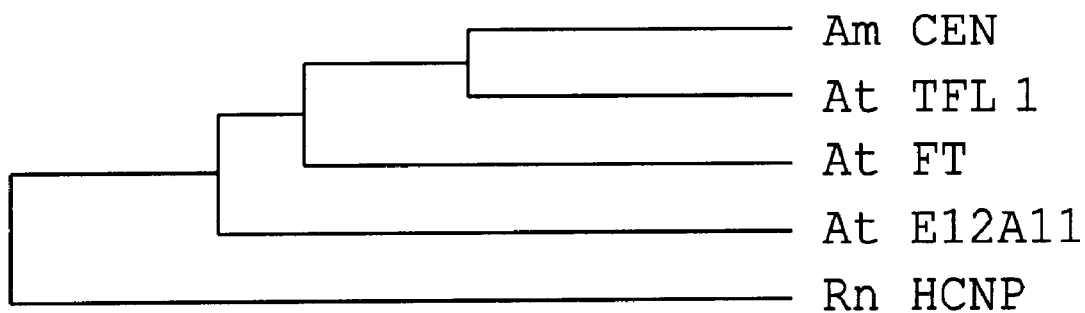
FIG. 3(A–C) shows sequence comparison of FT to related proteins in plants and mammals, with one-letter amino acid code. (A) shows a comparison of At FT (SEQ ID NO:4), At TFL1 (SEQ ID NO:5), At E12A11 (SEQ ID NO:6), and Rn HCNP (SEQ ID NO:7). (B) shows a phylogenetic tree of Am CEN, At TFL1, At FT, At E12A11 and Rn HCNP. (C) shows alignment of peptide sequences of At FT (SEQ ID NO:8), At TFL1 (SEQ ID NO:9), Am CEN (SEQ ID NO:10), At E12A 11 (SEQ ID NO:11), Rn HNCP (SEQ ID NO: 12); and Hs HNCP (SEQ ID NO:13).

FIG. 3B shows a phylogenetic tree, based on the alignment of protein sequences encoded by all five genes. Branch lengths reflect evolutionary distance. Am CEN and At TFL1 are proteins with orthologous function (Bradley et al., (1996) supra; Bradley et al., (1997) supra), and cluster together.

FIG. 3C shows alignment of HCNPs from rat and humans with the equivalent regions of plant proteins. Two of the three carboxy-terminal amino acids (proline-leucine), shown to be essential for HCNP activity (Ojika et al., (1996), *Neurosci. Lett.* 215, 127–30), are identical in all plant peptides, while the preceding amino acid is acidic (aspartate or glutamate) in plants, and glycine in mammals.

DETAILED DESCRIPTION

The present invention provides a gene that encodes a polypeptide that modulates flower development in plants. This gene, termed "FT" for flowering locus T, is useful for producing genetically modified plants characterized as having the phenotypic trait of modulated flower development, for example early or delayed flowering. Such plants can be genetically modified by at least a structural gene that encodes FT in order to modulate flowering in the plant.

Polypeptides, Polynucleotides and Vectors

The invention provides a substantially purified flowering locus T (FT) polypeptide and polynucleotides encoding FT. FT of the invention is characterized as having a molecular weight of approximately 20 kD, as determined by SDS-PAGE, being located on chromosome 1 of Arabidopsis, and functioning to modulate flowering time.

In one embodiment, the invention provides substantially purified FT polypeptide. Preferably, FT has an amino acid sequence set forth in SEQ ID NO:2. The term "substantially purified" as used herein refers to a polypeptide which is substantially free of other proteins, lipids, carbohydrates or other materials with which it is naturally associated. One skilled in the art can purify FT using standard techniques for protein purification. The substantially pure polypeptide will yield a single major band on a non-reducing polyacrylamide gel. The purity of the FT polypeptide can also be determined by amino-terminal amino acid sequence analysis.

The invention includes polypeptides having substantially the same as the amino acid sequence set forth in SEQ ID NO:2 or functional fragments thereof, or amino acid sequences that are substantially identical to SEQ ID NO:2. By "substantially the same" or "substantially identical" is meant a polypeptide or nucleic acid exhibiting at least 80%, preferably 85%, more preferably 90%, and most preferably 95% homology to a reference amino acid or nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 50 nucleotides, preferably at least 60 nucleotides, more preferably at least 75 nucleotides, and most preferably 110 nucleotides. FT homologs having substantially the same sequence as FT can be identified using the phylogenetic tree as shown in FIG. 3B, for example. FT homologs would map closer to FT than to TFL1/CEN, for example.

Functional fragments include those fragments of FT that retain the function or activity of FT, such as the ability to accelerate flowering. An example of such a peptide is shown in SEQ ID NO:4, and more specifically in SEQ ID NO:6 (plant-derived peptide). One of skill in the art can screen for the functionality of a fragment by using the examples provided herein, where full-length FT is described (e.g., see Example 3 for transgenic plants). It is also envisioned that fragments of FT that inhibit or delay flowering can be identified in a similar manner.

By "substantially identical" is also meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein assayed, (e.g., as described herein). Preferably, such a sequence is at least 85%, more preferably identical at the amino acid level to SEQ ID NO:2.

Homology is often measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, substitutions, and other modifications.

By a "substantially pure polypeptide" is meant an FT polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, FT polypeptide. A substantially pure FT polypeptide may be obtained, for example, by extraction from a natural source (e.g., a plant cell); by expression of a recombinant nucleic acid encoding an FT polypeptide; or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

Minor modifications of the FT primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the FT still exists. For example, the invention provides peptides of FT that have the biological activity of FT polypeptide. An exemplary FT peptide is shown in SEQ ID NO:4 (AADISQWAGPL), and more specifically in SEQ ID NO:6 (SINIRDPL) (see FIG. 3C for the Rn HNCP and At FT peptide sequences, respectively; At—*Arabidopsis thaliana*; Rn—*Rattus norvegicus* (rat)).

The polypeptides of the invention also include dominant negative forms of the FT polypeptide which do not have the biological activity of FT. A "dominant negative form" of FT is a polypeptide that is structurally similar to FT but does not have wild-type FT function. For example, a dominant-negative FT polypeptide may interfere with wild-type FT function by binding to, or otherwise sequestering, regulating agents, such as upstream or downstream components, that normally interact functionally with the FT polypeptide.

The invention provides polynucleotides encoding the FT protein. These polynucleotides include DNA, cDNA and RNA sequences which encode FT. It is understood that all polynucleotides encoding FT are also included herein, as long as they encode a polypeptide with FT activity. Such polynucleotides include naturally occurring, synthetic, and intentionally manipulated polynucleotides. For example, FT polynucleotide may be subjected to site-directed mutagenesis. The polynucleotide sequence for FT also includes antisense sequences, sequences encoding dominant negative forms of FT, and sequences encoding FT peptides, such as SEQ ID NO:4, and more specifically in SEQ ID NO:6. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of FT polypeptide encoded by the nucleotide sequence is functionally unchanged.

Specifically disclosed herein is a polynucleotide sequence containing the FT gene. Preferably, the FT nucleotide sequence is SEQ ID NO:1 from nucleotide base 37 to 849. The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g. a cDNA) independent of other sequences. The nucleotides of the invention can be ribonucleotides, deoxyribonucleotides, or modified forms of either nucleotide. The term includes single and double forms of DNA.

A "substantially identical" nucleic acid sequence codes for a substantially identical amino acid sequence as defined above.

By "purified DNA" or "isolated DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

The polynucleotide encoding FT includes SEQ ID NO:1 from nucleotide base 37 to 849, dominant negative forms of FT, and nucleic acid sequences complementary to SEQ ID NO: 1 from nucleotide base 37 to 849. A complementary sequence may include an antisense nucleotide. When the sequence is RNA, the deoxynucleotides A, G, C, and T of SEQ ID NO:1 from nucleotide base 37 to 849 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:2 under physiological conditions or a close family member of FT. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

The nucleotide sequence encoding the FT polypeptide of the invention includes the disclosed sequence and conservative variations thereof The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

DNA sequences encoding FT can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the FT polynucleotide sequences may be inserted into an expression vector. The term "expression vector" refers to a plasmid, virus or other vehicle known in the art that has been manipulated by insertion or incorporation of the FT genetic sequences. Polynucleotide sequence which encode FT can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., 1987, Methods in Enzymology 153:516–544). The expression of structural genes employed in the present invention may be driven by a number of promoters. Although the endogenous promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., *Nature*, 310:511, 1984; Odell, et al., *Nature*, 313:810, 1985); the full-length transcript promoter from Figwort Mosaic Virs (FMV) (Gowda, et al., *J. Cell Biochem.*, 13D: 301, 1989) and the coat protein promoter of TMV (Takamatsu, et al., *EMBO J.* 6:307, 1987). Alternatively, plant promoters such as the light-inducible promoter from the small subunit of ribulose bis-phosphate carboxylase (ssRUBISCO) (Coruzzi, et al., *EMBO J.*, 3:1671, 1984; Broglie, et al., *Science*, 224:838, 1984); mannopine synthase promoter (Velten, et al., *EMBO J.*, 3:2723, 1984), nopaline synthase (NOS) and octopine synthase (OCS) promoters (carried on tumor-inducing plasmids of *Agrobacterium tumefaciens* and have plant activity); ethylene inducible promotor whose level of activity is increased in response to treatment with ethylene or an equivalent compound such as propylene; heat shock promoters, e.g., soybean hsp17.5-E or hsp17.3-B (Gurley, et al., *Mol. Cell. Biol.*, 6:559, 1986; Severin, et al., *Plant Mol. Biol.*, 15:827, 1990); or ethanol-inducible promoters (Caddick et al., *Nature Biotech.*, 16:177, 1998) may be used.

Promoters useful in the invention include both constitutive and inducible natural promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., *Proc. Natl. Acad. Sci., U.S.A.*, 90:4567, 1993); In2-1 and In2-2 regulator sequences which are activated by substituted benzenesulfonamides, e.g., herbicide safeners (Hershey, et al., *Plant Mol. Biol.*, 17:679, 1991); the GRE regulatory sequences which are induced by glucocorticoids (Schena, et al., *Proc. Natl. Acad. Sci., U.S.A.*, 88:10421, 1991); and ethanol-inducible promoters (Caddick et al., supra). Other promoters, both constitutive and inducible and enhancers will be known to those of skill in the art.

The particular promoter selected should be capable of causing sufficient expression to result in the production of an effective amount of the structural gene product, e.g., FT to cause early flowering or antisense to cause late flowering. The promoters used in the vector constructs of the present invention may be modified, if desired, to affect their control characteristics. Tissue specific promoters may also be utilized in the present invention. As used herein, the term "tissue-specific promoter" means a DNA sequence that serves as a promoter, i.e., regulates expression of a selected DNA sequence operably linked to the promoter. A tissue-specific promoter effects expression of the selected DNA sequence in specific cells, e.g., in the root or in the shoot of a plant. The term also covers so-called "leaky" promoters, which regulate expression of a selected DNA primarily in one tissue, but cause expression in other tissues as well. Such promoters also may include additional DNA sequences that are necessary for expression, such as introns and enhancer sequences. An example of a tissue specific promoter is the HHA promoter expressed in shoot meristems (Atanassova, et al., *Plant J.*, 2:291, 1992). Other tissue specific promoters useful in transgenic plants, including the cdc2a promoter and cyc07 promoter, will be known to those of skill in the art. (See for example, Ito, et al., *Plant Mol. Biol.*, 24:863, 1994; Martinez, et al., *Proc. Natl. Acad. Sci. USA*, 89:7360, 1992; Medford, et al., *Plant Cell*, 3:359, 1991; Terada, et al., *Plant Journal*, 3:241, 1993; Wissenbach, et al., *Plant Journal*, 4:411, 1993). Examples of tissue specific promoters active in floral meristems are the promoters of the apetala 3 and apetala 1 genes which are described in Jack et al., *Cell*, 76:703, 1994 and Hempel et al., *Development* 124:3845, 1997. In addition, meristem-specific promoter from the UFO gene is included.

Optionally, a selectable marker may be associated with the heterologous nucleic acid sequence, i.e., the structural gene operably linked to a promoter. As used herein, the term "marker" refers to a gene encoding a trait or a phenotype which permits the selection of, or the screening for, a plant or plant cell containing the marker. The marker gene may be an antibiotic resistance gene whereby the appropriate antibiotic can be used to select for transformed cells from among cells that are not transformed or the marker gene may be herbicide resistance gene. Examples of suitable selectable markers include adenosine deaminase, dihydrofolate reductase, hygromycin-B-phosphotransferase, thymidine kinase, xanthine-guanine phospho-ribosyltransferase, glyphosphate and glufosinate resistance and amino-glycoside 3'-O-phosphotransferase II (kanamycin, neomycin and G418 resistance). Other suitable markers will be known to those of skill in the art.

Vector(s) employed in the present invention for transformation of a plant cell to modulate flower meristem development comprise a nucleic acid sequence comprising at least one structural gene encoding a protein that modulates flower meristem development, operably associated with a promoter. To commence a transformation process in accordance with the present invention, it is first necessary to construct a suitable vector and properly introduce it into the plant cell. The details of the construction of the vectors then utilized herein are known to those skilled in the art of plant genetic engineering. In the present invention, preferably the gene encoding a protein that modulates flower meristem development is the FT gene. The FT gene may be utilized alone or in combination with another structural gene, such as another gene which encodes a protein important in the development of flowering. Examples of such genes include LEAFY (LFY), APETALA1 (AP1), CONSTANS (CO), TERMINAL FLOWER1 (TFL1), FLORICAULA (FLO), SQUAMOSA (SQUA), FLOWERING LOCUS CA (FCA) and combinations thereof. It should be understood that all methods and plants described herein that the phrase "at least FT gene" or similar phrases include the use of one or more other flower development genes, such as those listed above or those known in the art.

For example, the heterologous nucleic acid sequences utilized in the present invention can be introduced into plant cells using Ti plasmids, root-inducing (Ri) plasmids, and plant virus vectors. (For reviews of such techniques see, for example, Weissbach & Weissbach, 1988, Methods for Plant Molecular Biology, Academic Press, NY, Section VIII, pp. 421–463; and Grierson & Corey, 1988, Plant Molecular Biology, 2d Ed., Blackie, London, Ch. 7–9, and Horsch, et al., Science, 227:1229, 1985, both incorporated herein by reference).

One of skill in the art will be able to select an appropriate vector for introducing the heterologous nucleic acid sequence in a relatively intact state. Thus, any vector which will produce a plant carrying the introduced DNA sequence should be sufficient. Even a naked piece of DNA would be expected to be able to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of a heterologous nucleic acid sequence. "Transformation" refers to the insertion of an exogenous polynucleotide into a host cell, irrespective of the method used for the insertion, for example, direct uptake, transduction, bombardment or electroporation. The exogenous polynucleotide may be maintained as a non-integrated vector, for example, a plasmid, or alternatively, may be integrated into the host genome.

One approach, known as direct transformation, induces uptake and integration of plasmid or linearized DNA in the genome of plant protoplasts, i.e., single cells stripped of cell wall material (Lorz et al., 1985, Mol. Genet. 199:178–182). Another approach involves the transfer of exogenous bacteriophage or plasmid DNA into germinating pollen grains to modify plant properties. As the pollen tube emerges from the mature pollen grain, cell wall material is deposited behind the growing tip.

A third approach relies on infection by Agrobacterium bacterium, which inserts sequences of a plasmid, known as the Ti-plasmid, into the genome of plant cells (Chilton et al., 1977, Cell 11:263:271). A heterologous nucleic acid sequence can be introduced into a plant cell utilizing *Agrobacterium tumefaciens* containing the Ti plasmid. In using an *A. tumefaciens* culture as a transformation vehicle, it is most advantageous to use a non-oncogenic strain of the Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, Biotechnology, 1:262, 1983; Hoekema, et al., Nature, 303:179, 1983). Such a binary system is preferred because it does not require integration into Ti plasmid in Agrobacterium.

Methods involving the use of Agrobacterium include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in situ transformation by Agrobacterium, as described by Bechtold, et al., (C. R. Acad. Sci. Paris, 316:1194, 1993). This approach is based on the vacuum infiltration of a suspension of Agrobacterium cells.

The preferred method of introducing heterologous nucleic acid into plant cells is to infect such plant cells, an explant, a meristem or a seed, with transformed *Agrobacterium tumefaciens* as described above. Under appropriate conditions known to those skilled in the art, the transformed plant cells are grown to form shoots, roots, and develop further into plants.

A preferred vector(s) of the invention comprises a Ti plasmid binary system wherein the heterologous nucleic acid sequence encodes the FT protein. Such a vector may optionally contain at least one other nucleic acid sequence which encodes a second flower development factor, such as LEAFY (LFY), APETALA1 (AP1), CONSTANS (CO), TERMINAL FLOWER1 (TFL1), FLORICAULA (FLO), SQUAMOSA (SQUA), FCA and combinations thereof. Alternatively, two vectors can be utilized wherein each vector contains at least one heterologous nucleic acid sequence. Other flower development genes can be utilized for construction of one or more vectors, in a similar manner.

Alternatively, heterologous nucleic acid can be introduced into a plant cell by contacting the plant cell using mechanical or chemical means. For example, the nucleic acid can be mechanically transferred by microinjection directly into plant cells by use of micropipettes. Alternatively, the nucleic acid may be transferred into the plant cell by using polyethylene glycol which forms a precipitation complex with genetic material that is taken up by the cell.

Heterologous nucleic acid can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of small beads or particles, or on the surface thereof (Klein, et al., Nature 327:70, 1987). Although, typically only a single introduction of a new nucleic acid sequence is required, this method particularly provides for multiple introductions.

Cauliflower mosaic virus (CaMV) may also be used as a vector for introducing heterologous nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

Methods for Producing Genetically Modified Plants

In another embodiment, the invention provides a method for genetically modifying a plant cell such that a plant, produced from the cell, is characterized as having modulated flower development as compared with a wild-type plant. The method includes introducing at least FT encoding polynucleotide of the invention into a plant cell to obtain a transformed plant cell and growing the transformed plant cell under conditions which permit expression of FT polypeptide, thereby producing a plant having modulated flower development. The term "modulated" refers to accelerated flower development or inhibited or delayed flower development.

Accelerated flower development can be achieved by induction or augmentation of FT gene expression or FT polypeptide activity. Vectors encoding FT polypeptide that are useful in the method of the invention are described herein. For example, FT gene expression under control of an inducible promoter or constitutive promoter can be used to increase FT expression over levels found in wild-type plants.

Similarly, inhibited flower development can be achieved by inhibiting FT gene expression or FT polypeptide activity in the plant. FT antisense or FT dominant negative nucleic acid sequences can be used to inhibit FT gene expression for example.

While the present examples demonstrate that constitutive expression of a floral regulatory gene (FT) causes accelerated flowering, and that expression of an antisense nucleic acid can be used to inhibit or delay flowering, this system could be modified such that flowering would be inhibited using dominant negative polypeptides. For example, dominant-negative versions of FT and/or other floral regulatory genes could be expressed constitutively. Dominant-negative mutants are proteins that actively interfere with the function of a normal, endogenous protein. Thus, the action of a gene can be blocked without inactivating the structural gene itself or its RNA. This strategy has been successful for both signal transduction molecules and for transcription factors (e.g., Attardi, et al., *Proc. Natl. Acad. Sci. USA*, 90:10563, 1993; Lloyd, et al., *Nature*, 352:635, 1991; Logeat, et al., *EMBO J.*, 10:1827, 1991: Mantovani, et al., *J. Biol. Chem.*, 269:20340, 1994; Ransone, et al., *Proc. Natl. Acad. Sci. USA*, 87:3806, 1990; Richardson, et al., *Mech. Dev.*, 45:173, 1994; Tsai, et al., *Genes Dev.*, 6:2258, 1992; Thomas et al., *Nature Genetics*, 17:58, 1997; Wittbrodt, J. And Rosa, F., *Genes and Development*, 8:1448, 1994; Kashles et al., *Mol. Cell. Biol.*, 11:1454, 1991; Pierce & Kimelman, *Development*, 121:755, 1995).

In another embodiment, the invention includes a method of producing a genetically modified plant characterized as having modulated flower meristem development, including contacting a plant cell with a vector, including a heterologous nucleic acid sequence comprising at least one structural gene encoding FT polypeptide, operably associated with a promoter to obtain a transformed plant cell; growing a plant from the transformed plant cell; and selecting a plant exhibiting modulated flower meristem development.

As used herein, the term "contacting" refers to any means of introducing the vector(s) into the plant cell, including chemical and physical means as described above. Preferably, contacting refers to introducing the nucleic acid or vector into plant cells (including an explant, a meristem or a seed), via *Agrobacterium tumefaciens* transformed with the heterologous nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part). Plant cell, as used herein includes, without limitation, algae, cyanobacteria, seeds, suspension cultures, embryos, meristematic regions, callus tissue, leaves, roots, shoots, gametophytes, sporophytes, pollen, and microspores.

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxin and cytokinins. It is sometimes advantageous to add glutamic acid and proline to the medium, especially for such species as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee, et al., *Annual Review of Plant Physiology*, 38:467, 1987). Utilizing the leaf disk-transformation-regeneration method of Horsch, et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by the taking of cuttings or by tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The inbred plant produces seed containing the newly introduced foreign gene(s). These seeds can be grown to produce plants that would produce the selected phenotype, e.g. early flowering.

Parts obtained from the regenerated plant, such as flowers, seeds, leaves, branches, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Plants exhibiting modulated flower development can be selected by visual observation. The invention includes a plant produced by the method of the invention, including plant tissue, seeds, and other plant cells derived from the genetically modified plant.

In yet another embodiment, the invention provides a method for modulating flower meristem development in a plant cell including contacting a plant cell with a vector as described above to obtain a transformed plant cell, growing the transformed plant cell under plant forming conditions, and modulating flower meristem development in the plant. The method of the invention requires that the promoter sequence operably linked with the structural gene. The promoter is an inducible promoter when induction of flower development is desired. For example, a plant cell and plant is produced as described above and modulated flower meristem development is induced by contacting the promoter, linked with a nucleic acid sequence encoding FT, with an appropriate inducer. Such inducible promoters are described above, and include those promoters preferably inducible by chemical means.

By "transformation" is meant a generic change induce in a cell following incorporation of new DNA (i.e. DNA exogenous to the cell). Where the cell is a mammalian cell, the genetic change is generally achieved by introduction of the DNA into the genome of the cell (i.e. stable). By "transformed cell" is meant a cell into which (or into an ancestor of which) has been introduced, by means of recombinant DNA techniques, a DNA molecule encoding FT. Transformation of a host cell with recombinant DNA may be carried out by conventional techniques as are well known to those skilled in the art.

Antibodies

The FT polypeptides of the invention can be used to produce antibodies which are immunoreactive or bind to epitopes of the FT polypeptides. Antibodies which consist essentially of pooled monoclonal antibodies with different epitopic specificities, as well as distinct monoclonal antibody preparations are provided.

The preparation of polyclonal antibodies is well-known to those skilled in the art. See, for example, Green et al., Production of Polyclonal Antisera, in: *Immunochemical Protocols* (Manson, ed.), pages 1–5 (Humana Press 1992); Coligan et al., Production of Polyclonal Antisera in Rabbits, Rats, Mice and Hamsters, in: *Current Protocols in Immunology*, section 2.4.1 (1992), which are hereby incorporated by reference.

The preparation of monoclonal antibodies likewise is conventional. See, for example, Kohler & Milstein, 1975, Nature 256:495; Coligan et al., sections 2.5.1–2.6.7; and Harlow et al., in: *Antibodies: a Laboratory Manual*, page 726 (Cold Spring Harbor Pub. 1988), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan et al., sections 2.7.1–2.7.12 and sections 2.9.1–2.9.3; Barnes et al., Purification of Immunoglobulin G (IgG), in: *Methods in Molecular Biology*, Vol. 10, pages 79–104 (Humana Press 1992).

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, e.g., syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

The term "antibody" as used in this invention includes intact molecules as well as fragments thereof, such as Fab, $F(ab')_2$, and Fv which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York (1988), incorporated herein by reference). As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. No. 4,036,945 and No. 4,331,647, and references contained therein. These patents are hereby incorporated in their entireties by reference. See also Nisonhoff et al., 1960, Arch. Biochem. Biophys. 89:230, Porter, 1959, Biochem. J. 73:119; Edelman et al., 1967, *Methods in Enzymology*, Vol. 1, page 422 (Academic Press); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar et al., 1972, Proc. Nat'l Acad. Sci. USA 69:2659. Alternatively, the variable chains can be linked by an intermolecular disulfide bond or cross-linked by chemicals such as glutaraldehyde. See, e.g., Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., 1991, *Methods: a Companion to Methods in Enzymology*, Vol. 2, page 97; Bird et al., 1988, Science 242:423–426; Ladner et al., U.S. Pat. No. 4,946,778; Pack et al., 1993, Bio/Technology 11:1271–77; and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: a Companion to Methods in Enzymology*, Vol. 2, page 106 (1991).

Antibodies which bind to the FT polypeptide of the invention can be prepared using an intact polypeptide or fragments containing small peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Genetically Modified Plants

In one embodiment, the invention provides a genetically modified plant comprising at least one heterologous nucleic acid sequence encoding FT in its genome, wherein the FT sequence modulates flowering in the plant. The plant is therefore characterized as having modulated flower development. Also included herein are plant cells and plant tissue, all derived from the genetically modified plant of the invention. In addition, seeds which can germinate into a genetically modified plant as described herein are also provided.

The term "genetic modification" as used herein refers to the introduction of one or more heterologous nucleic acid sequences into one or more plant cells, which can generate whole, sexually competent, viable plants. The term "genetically modified" as used herein refers to a plant which has been generated through one of the aforementioned processes. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any flowering plants amenable to transformation techniques, including both monocotyledonous and dicotyledonous plants.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Woody species include poplar, pine, sequoia, cedar, and oak.

The term "heterologous nucleic acid sequence" as used herein refers to at least one structural gene operably associated with a regulatory sequence such as a promoter. The nucleic acid sequence originates in a foreign species, or, in the same species if substantially modified from its original form. For example, the term "heterologous nucleic acid sequence" includes a nucleic acid originating in the same species, where such sequence is operably linked to a promoter that differs from the natural or wild-type promoter.

As used herein, the term "nucleic acid sequence" refers to a polymer of deoxyribonucleotides or ribonucleotides, in the form of a separate fragment or as a component of a larger construct. DNA encoding the proteins utilized in the method of the invention can be assembled from cDNA fragments or from oligonucleotides which provide a synthetic gene which is capable of being expressed in a recombinant transcriptional unit. Polynucleotide or nucleic acid sequences of the invention include DNA, RNA and cDNA sequences (see description previously).

Antisense Polynucleotides

Inhibition of flowering or delayed or late flowering can be achieved by introduction of antisense molecules into a plant cell from which a transformed or genetically modified plant is produced. This approach also includes, for example, antisense nucleic acid, ribozymes, or triplex agents to block transcription or translation of FT mRNA, either by masking that mRNA with an antisense nucleic acid or triplex agent, or by cleaving it with a ribozyme. An exemplary antisense polynucleotide of the invention is set forth in SEQ ID NO:3 (FIG. 2).

In one embodiment, the invention includes a genetically modified plant having a transgene disrupting or interfering with expression of flowering time gene (FT), chromosomally integrated into the genome of the plant. A "transgene" is any piece of DNA which is inserted by artifice into a cell, and becomes part of the genome of the organism or plant which develops from that cell. Such a transgene may include a gene which is partly or entirely heterologous (i.e., foreign) to the transgenic organism, or may represent a gene homologous to an endogenous gene of the organism. As used herein, the term "transgene" means a DNA sequence that includes one or more selected DNAs to be expressed in a genetically modified or transgenic plant which is partly or entirely heterologous, i.e., foreign, to the transgenic plant, or homologous to an endogenous gene of the transgenic plant, but which is designed to be inserted into the plant's genome at a location which differs from that of the natural gene. A transgene includes one or more promoters and any other DNA, such as introns, necessary for expression of the selected DNA, all operably linked to the selected DNA, and may include an enhancer sequence.

The invention includes a method of producing a genetically modified plant characterized as having late flower development by contacting a plant cell with a vector containing a nucleic acid sequence including at least a structural gene disrupting or interfering with expression of FT polypeptide, wherein the gene is operably associated with a promoter, to obtain a transformed plant cell; producing a plant from the transformed plant cells; and selecting a plant exhibiting late flower development. Late flower development can be identified as demonstrated in the Examples herein, e.g., visual observation of transgenic plant flowering time versus wild-type plant flowering time. Flowering time can be determined by counting the number of leaves before a first flower is produced (Koornneef et al., *Mol. Gen. Genet.*, 229:57, 1991). Other indicators include detection of promoter activity of floral-meristem identity genes, such as LEAFY or APETALA 1 (Blazquez et al., *Development*, 124:3835, 1997; Hempel, supra).

The method of producing a genetically modified plant characterized as having late flower development includes contacting a plant cell with a vector containing an FT antisense nucleic acid sequence or a nucleic acid sequence encoding a dominant negative form of FT, operably associated with a promoter. The antisense nucleic acid sequence of SEQ ID NO:3, provided herein, was utilized as shown in EXAMPLE 3, to produce genetically modified plants having late flower development as compared to wild-type plants.

Antisense nucleic acids are DNA or RNA molecules that are complementary to at least a portion of a specific mRNA molecule (Weintraub, 1990, Scientific American, 262:40). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target FT-producing cell. The use of antisense methods to inhibit the in vitro translation of genes is well known in the art (Marcus-Sakura, 1988, Anal.Biochem., 172:289). Virus can also be used for antisense suppression (Angell and Balcombe, *EmboJ.*, 16:3675, 1997).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., 1991, Antisense Res. and Dev., 1(3):227; Helene, C., 1991, Anticancer Drug Design, 6(6):569).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, 1988, J.Amer.Med. Assn., 260:3030). A major advantage of this approach is that, because they are sequence-specific, only mRNAs with particular sequences are inactivated.

There are two basic types of ribozymes namely, tetrahymena-type (Hasselhoff, 1988, Nature, 334:585) and "hammerhead"-type. Tetrahymena-type ribozymes recognize sequences which are four bases in length, while "hammerhead"-type ribozymes recognize base sequences 11–18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Dominant Negative Mutations

In another embodiment of the present invention, a nucleotide sequence encoding a FT dominant negative protein is provided. For example, a genetic construct that contain such a dominant negative encoding gene may be operably linked to a promoter, such as a tissue-specific promoter. Examples of such promoters and methods of use are described above.

Such constructs are useful in methods of modulating flower development in a plant. For example, a method of the invention includes transforming a plant cell or tissue with a genetic construct encoding a dominant negative FT protein and suitable promoter in operable linkage and expressing the dominant negative encoding FT gene, thereby modulating flower development by interfering with wild-type FT activity.

Screen for FT Inhibitors

In another embodiment, the invention provides a method for identifying a compound which modulates FT protein activity or gene expression. The method includes incubating components comprising the compound, FT polypeptide or a recombinant cell expressing FT polypeptide, under conditions sufficient to allow the components to interact and determining the effect of the compound on FT activity or expression. The effect of the compound on FT activity can be measured by a number of assays, and may include measurements before and after incubating in the presence of the compound. Compounds that affect FT activity or gene expression include peptides, peptidomimetics, polypeptides, chemical compounds and biologic agents. Assays include Northern blot analysis of FT mRNA (e.g., for gene expression) and Western blot analysis (e.g., for protein activity).

Incubating includes conditions which allow contact between the test compound and FT polypeptide or with a recombinant cell expressing FT polypeptide. Contacting includes in solution and in solid phase, or in a cell. The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology*, 3:1008–1012, 1985), allele-specific oligonucleotide (ASO) probe analysis (Conner, et al., *Proc. Natl. Acad. Sci. USA*, 80:278, 1983), oligonucleotide ligation assays (OLAs) (Landegren, et al., *Science*, 241:1077, 1988), and the like. Molecular techniques for DNA analysis have been reviewed (Landegren, et al., *Science*, 242:229–237, 1988).

Method for Identifying Compounds that Affect FT

The invention provides a method for identifying a compound which can modulate a FT activity. The method includes incubating FT polypeptide or a recombinant cell expressing a FT polypeptide or variant thereof, and a test compound, under conditions sufficient to allow the components to interact, and measuring the effect of the compound on the activity or expression of FT. Compounds that affect FT activity or gene expression include peptides, polypeptides, pepidomimetics, chemical compounds and biological agents.

"Incubating" includes conditions which allow contact between the test compound and FT polypeptide. "Contacting" includes in solution and solid phase. The test compound may also be a combinatorial library for screening a plurality of compounds. A variety of other agents may be included in the screening assay. These include agents like salts, neutral proteins, e.g., albumin, detergents, etc that are used to facilitate optimal protein-protein binding and/or reduce nonspecific or background interactions. Reagents that improve the efficiency of the assay, such as protease inhibitors, nuclease inhibitors, anti-microbial agents, etc., may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 10 hours will be sufficient.

Compounds that are nucleic acid in nature identified in the method of the invention can be further evaluated, detected, cloned, sequenced, and the like, either in solution of after binding to a solid support, by any method usually applied to the detection of a specific DNA, such as PCR, oligomer restriction (Saiki et al., 1985, *Bio/Technology*, 3:1008–1012), allele-specific oligonucleotide (ASO) probe analysis (Conner et al.,1983, *Proc. Natl. Acad. Sci. USA*, 80:278), oligonucleotide ligation assays (OLAs) (Landegren et al., 1988, *Science*, 241:1077), and the like. Molecular techniques for DNA analysis have been reviewed (Landegren et al., 1988, *Science*, 242:229–237).

Candidate compounds that affect FT include chemical comounds. One class is organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups.

Candidate compounds are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc., to produce structural analogs. Candidate agents are also found among biomolecules including, but not limited to: peptides, saccharides, fatty acids, steroids, purines, pyrimidines, derivatives, structural analogs or combinations thereof.

A compound can affect reporter gene expression by either stimulating or inhibiting the expression of the reporter gene. A compound "inhibits" reporter gene expression if the level of transcripts or protein product produced from the reporter gene is decreased as compared with the level in the absence of the test compound. A compound "stimulates" reporter gene expression if the if the level of transcripts or protein product produced from the reporter gene is increased.

One of skill in the art can identify a number of reporter genes for use in the screening method of the invention. Examples of reporter genes of use with the invention are lacZ, luciferase, chloramphenicol acetyltransferase, beta-glucuronidase and green fluorescent protein.

The effect of the compound on the reporter gene transcription can be measured by assessing the expression of the reporter by methods well known in the art (e.g., Northern blots; EMSA). Alternatively or the production of protein product from the reporter gene can be measured by methods well known in the art (e.g., ELISA or RIA; Western blots; SDS-PAGE).

The invention further provides a method for identifying a cellular protein that binds to FT polypeptide or a variant thereof, by incubating at least one cellular protein and FT polypeptide or a variant thereof under conditions sufficient for the components to interact, and separating a complex of the FT polypeptide and a putative binding protein from the unbound FT, and isolating the protein (e.g., a 2-hybrid system).

In a preferred embodiment, an isolated cellular protein is utilized. However, partially purified proteins, fractions of cell extracts, whole cell extracts, or intact cells may be utilized with the method of the invention. "Incubating" includes conditions which allow contact between the cellular component and the FT polypeptide. The term "interact" includes in solution and solid phase, and includes any complex formation or binding of the cellular component to the FT polypeptide. Interact also includes any enzymatic interaction wherein the cellular component performs a biochemical modification of the FT polypeptide.

The complex of the cellular component with a FT polypeptide can be separated from uncomplexed FT polypeptide by conventional means, well known to one of skill in the art. The presence of cellular component bound to FT can be accomplished by size separation, physical separation, or other standard methods. For example, nondenaturing gel electrophoresis can be used to separate FT complexed with a cellular component from uncomplexed FT.

Once the complex has been isolated, the cellular component can be isolated and characterized by means well known in the art. For example, if the cellular component is a protein, the protein can be sequenced using methodology well known in the art. Polynucleotide encoding the protein can be produced using DNA synthesis technology. The polynucleotide can then be inserted into a vector using or molecular techniques well known in the art, and transformed into host cells using the techniques described above. Following transformation, large amounts of the protein may be isolated and purified in accordance with conventional ways. For example, lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The above disclosure generally describes the present invention. A more complete understanding can be obtained by reference to the following specific examples which are provided herein for purposes of illustration only and are not intended to limit the scope of the invention.

EXAMPLE 1

Identification of FT

Figure 1:
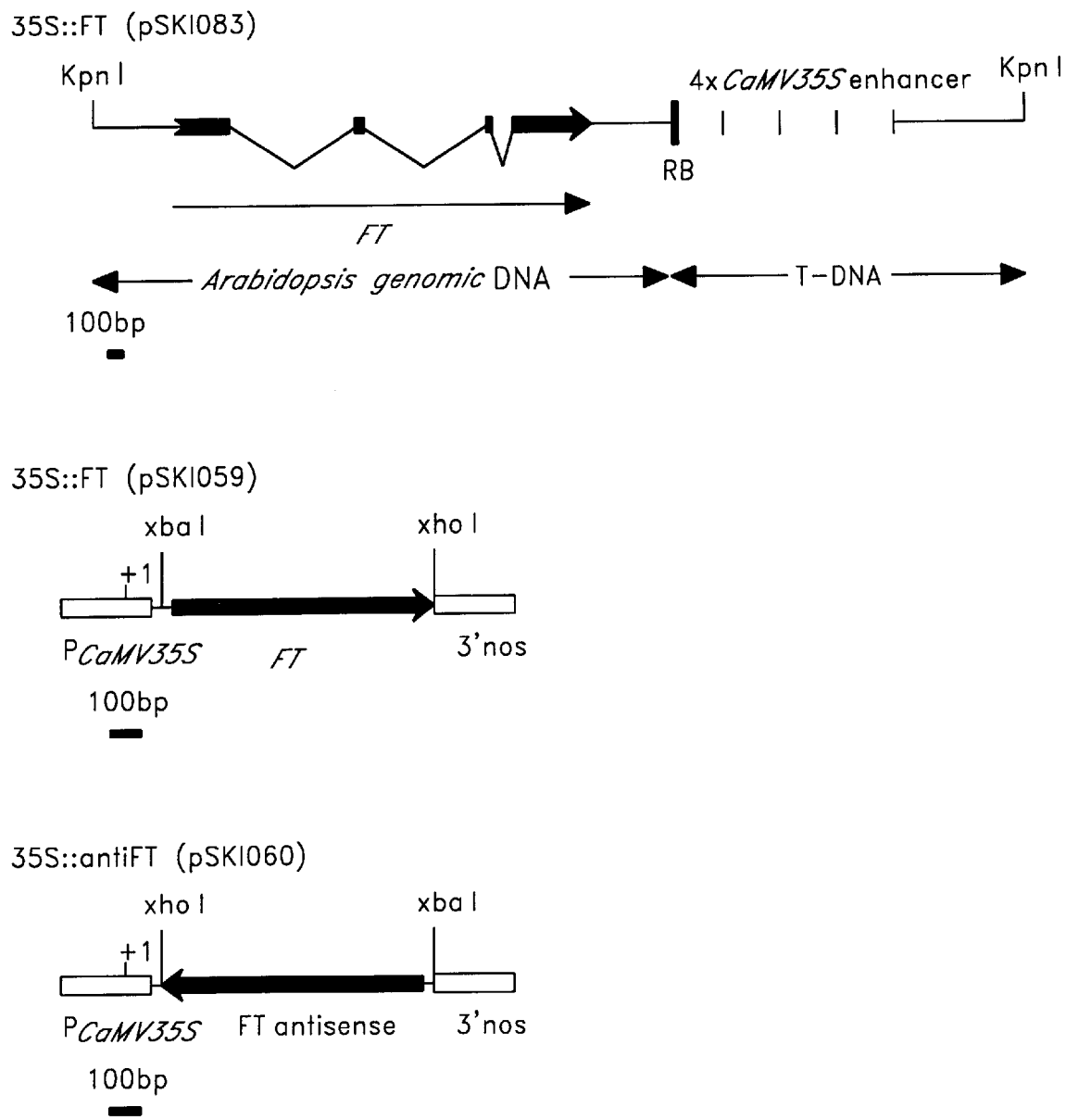
FIG. 1 shows partial maps of T-DNA vector inserts. For pSKI083, the Kpn I fragment isolated from the original 1733 line is shown. This fragment contains the genomic region that gives rise to the FT transcripts, the right border (RB) of the original T-DNA insertion, as well as the tetramer of CaMV35S enhancer sequences derived from the original activation-tagging vector. FT exons are drawn as boxes, and introns as thin lines. 3' and 5' untranslated regions are indicated by shading, and the translated region by solid black. For pSKI059 and pSKI060, the Xba 1/Xho 1 fragment spanning the FT cDNA is shown along with its orientation with respect to the CaMV35S promoter and 3' nos sequences is shown. +1 indicates the transcription start.

During the past years, we have used the vacuum-infiltration method (Bechtold et al., (1993), *C. R. Acad. Sci.* 316, 1194–1199) to generate a large number of *Arabidopsis thaliana* plants transformed with an activation-tagging T-DNA vector. This vector contains a tetramer of the strong cauliflower mosaic virus 35S enhancer next to the right border of the T-DNA, as described by Walden and colleagues (1994), *Plant Mol. Biol.* 26, 1521–1528). From our population of transformed plants, we identified a line that contained a dominant, heritable mutation conferring very early flowering independently of environmental conditions. This line, 1733, flowered with an average of 3.5 leaves in both long and short days, while wild-type plants flowered with an average of 13 and 45 leaves, respectively. After we had confirmed that the dominant phenotype co-segregated with the activation-tagging vector, we isolated flanking sequences by plasmid rescue. A fragment containing 3.4 kb of genomic sequence along with the multimerized enhancer from the original vector was inserted into another T-DNA vector, to yield plasmid pSKI083 (FIG. 1). This construct was introduced again into plants by vacuum infiltration.

A large number of pSKI083 transformed plants had the same phenotype as the original mutant line, demonstrating that the pSKI083 fragment contained the gene conferring early flowering. The pSKI083 fragment was mapped by hybridization to an arrayed yeast artificial chromosome library, and a map position determined at the bottom of chromosome 1. The only flowering-time gene known to be located in this area was the FT gene, whose recessive alleles cause late flowering (Koornneef et al., (1991), *Mol. Gen. Genet.* 229, 57–66). The structural gene encoding the FT locus had not been previously isolated. Genomic DNA from three independent, EMS-induced ft alleles was sequenced, and found that all of them contained single base pair changes that introduced either missense mutations or stop codons into the single gene contained on this genomic fragment (see below). Thus, the original activation-tagged mutant was a dominant, early-flowering allele at the FT locus, whose inactivation causes an opposite phenotype, late flowering.

EXAMPLE 2

FT Sequence and Relation to Other Genes

We determined the sequence of the genomic fragment on pSKI083 as well as the sequence of cDNAs originating from this fragment (FIGS. 1, 2). The FT cDNA contains a single open reading frame, predicted to produce a protein that is 175 amino acids long, has a molecular weight of 19.8 kD, and an isoelectric point of 7.89.

Database searches revealed that FT is a member of a gene family that is represented in plants, fungi and mammals. Functional information was available for a pair of orthologous genes from plants, and another pair of orthologous genes from mammals (FIG. 3A). The two plant genes are CENTRORADIALIS (CEN) from snapdragon (*Antirrhinum majus*) and TERMINAL FLOWER 1 (TFL1) from *Arabidopsis thaliana* (Bradley et al., 1996, supra; Bradley et al., 1997, supra). Inactivation of these genes by mutation causes the formation of terminal flowers on both main and lateral shoots.

In addition, tfl1 mutants flower slightly early when compared to wild type (Shannon and Meeks-Wagner, (1991), *Plant Cell* 3, 877–892). We have recently generated plants in which TFL1 is overexpressed (35S::TFL1), and these plants flower late. Thus, the TFL1 gene, which is related in sequence to FT, plays a role in flowering that is opposite to that of FT. FT overexpressers flower early, and so do tfl1 loss-of-function mutants. Conversely, ft loss-of-function mutants flower late, and so do TFL1 overexpressers.

The *Arabidopsis thaliana* genome contains at least one other member of the FT/TFL1 gene family. This gene has been identified as an anonymous expressed sequence tag (EST clone #E12A11), with the GenBank accession number AA042630. We have determined the complete sequence of the E12A11 cDNA (FIG. 3A). In contrast to FT and TFL1, overexpression of this gene in transgenic plants (35S::E12A11) does not appear to affect flowering.

A phylogenetic tree of the protein sequences of CEN, TFL1, FT and E12A11 shows that TFL1 is more closely related to CEN, which is from a different species, than to FT and E12A11, which are from the same species as TFL1. The closer relationship between TFL1 and CEN compared to FT and E12A11 confirms that the former are orthologous genes (FIG. 3B). Furthermore, the sequence comparison shows that FT is more related to CEN/TFL1 than to E12A11. The phylogenetic tree provides thus an important criterion for identifying FT orthologs in other species. Such orthologs should be more related to FT from *Arabidopsis thaliana* than to either CEN/TFL1 or E12A11.

Two members of the FT/TFL1 family from mammals are the genes encoding the rat and human precursor proteins for hippocampal cholinergic neurostimulating peptide (Tohdoh et al., supra) (FIG. 3). The rat protein has been identified as a precursor protein, which gives rise to a peptide hormone that stimulates acetylcholine synthesis in a culture system of brain explants (Ojika et al., supra). The active principle, called HCNP, for hippocampal cholinergic neurostimulating peptide, had previously been purified and shown to be the eleven amino acid long peptide acetyl-Ala-Ala-Asp-Ile-Ser-Gln-Trp-Ala-Gly-Pro-Leu (SEQ ID NO:12) (FIG. 3C). The precursor protein was cloned, using DNA sequences predicted from the peptide sequence. The active peptide was shown to be generated by N-terminal cleavage, along with removal of the methionine and acetylation. However, acetylation is not essential for activity, and both acetylated and free HCNP have been found in vivo (Ojika et al., supra). The gene encoding human HCNP precursor protein has also been cloned. While the rat and human genes are overall very similar, only six out of the eleven amino acids of the predicted amino-terminal peptides are identical. However, both are effective in stimulating acetylcholine synthesis in rat medial septal nuclei cultures. When the bioactivity of short peptides containing human or rat HCNP sequences was tested, only tetrapeptides and hexapeptides including the carboxy-terminus of HCNP were found to be active. Based on sequence alignment, the minimum consensus sequence for HCNP activity was deduced to be X-Gly-Pro-Leu (Ojika et al., 1996).

While the amino termini of the plant proteins are rather diverged, all share the sequence (Asp or Glu)-Pro-Leu (FIG.

3C). If cleavage of the plant proteins occurs similar to HCNPs after the conserved leucine, the predicted plant peptides would be between seven and eleven amino acids long (FIG. 3C). The sequence similarities suggest strongly that the plant proteins act also as precursors for peptides that affect flowering. Thus, we predict that in addition to overexpression or inactivation of FT, application or overexpression of the FT peptide only will be useful to affect flowering time.

EXAMPLE 3

Transgenic Plants that Overexpress FT in Sense and Antisense Orientation

Using as a probe the genomic DNA fragment isolated by plasmid rescue, we obtained more than 10 cDNA clones from an *Arabidopsis thaliana* flower cDNA library (Weigel et al., 1992, *Cell* 69, 843–859). The cDNA clones were sequenced and found to all originate from the same gene. Clone pSKI1.1.1 was selected as containing a complete open reading frame, as well as 5' and 3' untranslated sequences, spanning 1814 bp. Partial maps of some of the recombinant DNA constructs described are given in FIG. 1, and the actual sequences of the sense (SEQ ID NO:5) and the antisense inserts (SEQ ID NO:3) are presented in FIG. 2.

For plant transformation, we constructed the pSKI090 binary T-DNA vector, which contains within its T-DNA borders the BAR gene conferring resistance to the herbicide glufosinate (BASTA™ or Ignite™) along with multiple cloning sites between a strong plant virus-derived synthetic promoter/translational enhancer (containing 200 bp of the cauliflower mosaic virus 35S promoter (Odell et al., (1985), Identification of DNA-sequences required for activity of the cauliflower mosaic virus-35S promoter. *Nature* 313, 810–812) and 70 bp of the 5' omega region of tobacco mosaic virus (Sleat et al., (1987), *Gene* 60, 217–225) and a transcriptional terminator from the Agrobacterium nopaline synthetase (nos) gene (see FIG. 1). Two intermediate steps in the generation of pSKI090 were the pBluescriptKS+ (Stratagene) derived vector pSKI087, which contains CaMV35S promoter and 3' nos sequences, and the T-DNA vector pSKI089, which contains the BAR gene.

To make the sense construct, the cDNA insert of clone pSKI1.1.1 was excised as an Xba I-XhoI fragment, subcloned into pSKI087, giving construct pSKI053; excessive polylinker sequence was removed by digestion with BamHI and religation, giving construct pSKI058; and finally the fragment containing synthetic promoter, FT cDNA and nos terminator was inserted into pSKI089 vector to yield pSKI059 (FIG. 1). Transgenic plants transformed with pSKI059 are expected to overproduce the FT mRNA.

To make the antisense construct, the cDNA insert of clone pSKI1.1.1 was excised as a Kpn I-Xba I fragment, and ligated with the suitably digested pSKI090 vector DNA (see FIG. 1), giving construct pSKI060. In this construct the FT open reading frame is in the opposite orientation to the synthetic promoter with regard to normal direction of transcription. pSKI059 (35S::FT) and pSKI060 (35S::antiFT) were mobilized into *Agrobacterium tumefaciens* strain ASE (Fraley et al., (1985), The SEV system: a new disarmed Ti plasmid vector system for plant transformation. *Biotechnology* 3, 629–635). The constructs were introduced into *Arabidopsis thaliana* ecotype Columbia by vacuum infiltration (Bechtold et al., 1993). Transgenic plants were selected by repeated spraying of young seedlings with a 1:10,000 dilution of Ignite™. For pSKI060 (35S::antiFT), we analyzed 50 transformants, of which 2 were late-flowering, producing greater than 25 rosette leaves (compared to wild type with 13 leaves).

For pSKI059 (35S::FT), we analyzed 50 transformants, of which 45 flowered much earlier than wild-type, with 9 of them being as early as the original 1733 mutant (3.5 versus 13 leaves).

FT may also act as a competence factor for LEAFY (Ruiz-Garcia et al., *Plant Cell*, 9:1921, 1997). We have crossed 35S::FT and 35S::LFY by standard methods and observed a synergistic effect. In other words, these plants flowered without making any vegetative leaves.

The foregoing is meant to illustrate, but not to limit, the scope of the invention. Indeed, those of ordinary skill in the art can readily envision and produce further embodiments, based on the teachings herein, without undue experimentation. Accordingly, the invention is limited only by the following claims.

What is claimed is:

1. An isolated polynucleotide encoding a flowering locus T (FT) polypeptide, said polypeptide comprising an amino acid sequence with at least 80% sequence homology to SEQ ID NOS:2 or 4, and wherein said polynucleotide encodes an amino acid sequence having the same functional activity as the amino acid sequence of SEQ ID NOs: 2 or 4.

2. The polynucleotide of claim 1, wherein the amino acid has at least 85% homology to SEQ ID NOS:2 or 4.

3. The polynucleotide of claim 1, wherein the amino acid has at least 90% homology to SEQ ID NOS:2 or 4.

4. The polynucleotide of claim 1, wherein the amino acid has at least 95% homology to SEQ ID NOS:2 or 4.

5. The polynucleotide of claim 1, wherein the amino acid has the sequence of SEQ ID NOS:2 or 4.

6. The polynucleotide of claim 1, wherein the polynucleotide has the sequence of SEQ ID NO: 1.

7. An isolated polynucleotide selected from the group consisting of:
   a) SEQ ID NO:1 from nucleotide base 37 to 849;
   b) SEQ ID NO:1 from nucleotide base 37 to 849, wherein T is optionally U;

c) nucleic acid sequences complementary to SEQ ID NO:1; and fragments of a), b), and c) that are at least 15 bases in length and that will specifically hybridize at high stringency conditions to nucleic acid sequences which encode the polypeptide of SEQ ID NO:2.

8. A recombinant expression vector comprising a polynucleotide sequence according to claim 1.

9. A bacterial or plant host cell comprises the vector of claim 8.

10. A genetically modified plant comprising at least one exogenous nucleic acid sequence encoding a FT-polypeptide, wherein said polypeptide comprises an amino acid sequence with at least 80% sequence homology to SEQ ID NOS:2 or 4, and wherein said exogenous nucleic acid sequence encodes an amino acid sequence having the same functional activity as the amino acid sequence of SEQ ID NOs:2 or 4.

11. The genetically modified plant of claim 10, wherein the amino acid comprises at least 85% homology to SEQ ID NOS:2 or 4.

12. The genetically modified plant of claim 10, wherein the amino acid comprises at least 90% homology to SEQ ID NOS:2 or 4.

13. The genetically modified plant of claim 10, wherein the amino acid comprises at least 95% homology to SEQ ID NOS:2 or 4.

14. The genetically modified plant of claim 10, wherein the amino acid comprises the sequence of SEQ ID NOS:2 or 4.

15. The genetically modified plant of claim 10, further comprising an exogenous gene encoding a polypeptide selected from the group consisting of LEAFY (LFY), APETALA1 (AP1), CONSTANS (CO), FLORICAULA (FLO), SQUAMOSA (SQUA), FLOWERING LOCUS CA (FCA) and combinations thereof.

16. The genetically modified plant of claim 10, wherein the exogenous nucleic acid sequence comprises a regulatory nucleic acid sequence.

17. The genetically modified plant of claim 16, wherein the regulatory nucleic acid sequence is a promoter.

18. The genetically modified plant of claim 17, wherein the promoter is a constitutive promoter.

19. The genetically modified plant of claim 17, wherein the promoter is an inducible promoter.

20. The genetically modified plant of claim 10, wherein the exogenous nucleic acid sequence further comprises a selectable maker.

21. The genetically modified plant of claim 10, wherein the plant is a dicotyledonous plant.

22. The genetically modified plant of claim 10, wherein the plant is a monocotyledonous plant.

23. A plant cell derived from the plant of claim 10.

24. Plant tissue derived from the genetically modified plant of claim 10.

25. A seed which germinates into a plant comprising at least one exogenous nucleic acid sequence encoding a FT-polypeptide, wherein said polypeptide comprises an amino acid sequence with at least 80% sequence homology to SEQ ID NOS:2 or 4, and wherein said nucleic acid encodes an amino acid sequence having the same functional activity as the amino acid sequence of SEQ ID NOs:2 or 4.

26. A vector comprising at least one nucleic acid encoding a FT polypeptide that accelerates flower development, said nucleic acid being operably associated with a promoter, wherein the FT polypeptide comprises a sequence as set forth in SEQ ID NOS:2, or 4.

27. The vector of claim 26, wherein the vector comprises a T-DNA derived vector.

28. The vector of claim 26, further comprising a structural gene encoding a polypeptide selected from the group consisting of LEAFY (LFY), APETALA1 (AP1), CONSTANS (CO), FLORICAULA (FLO), SQUAMOSA (SQUA), FLOWERING LOCUS CA (FCA) and combinations thereof.

29. The vector of claim 26, wherein the promoter is a constitutive promoter.

30. The vector of claim 26, wherein the promoter is an inducible promoter.

31. The vector of claim 26, wherein the promoter is induced by chemical means.

32. A method for genetically modifying a plant cell comprising:
  introducing at least one FT encoding polynucleotide of claim 1 into a plant cell to obtain a transformed plant cell.

33. A method of producing a genetically modified plant characterized as having early flower development, said method comprising:
  contacting a plant cell with a vector comprising a nucleic acid sequence encoding the amino acid sequence as set forth in SEQ ID NOs:2, or 4, said nucleotide sequence being operably associated with a promoter;
  producing a plant from said transformed plant cells; and
  selecting a plant exhibiting said early flower development.

34. The method of claim 33, wherein the contacting is by physical means.

35. The method of claim 33, wherein the contacting is by chemical means.

36. The method of claim 33, wherein the plant cell is selected from the group consisting of protoplasts, gamete producing cells, and cells which regenerate into a whole plant.

37. The method of claim 33, wherein the promoter is a constitutive promoter.

38. The method of claim 33, wherein the promoter is an inducible promoter.

39. A plant produced by the method of claim 33.

40. Plant tissue of a plant produced by the method of claim 33.

41. An isolated polynucleotide encoding a flowering locus T (FT) polypeptide, wherein said polynucleotide hybridizes to the nucleic acid sequence of SEQ ID NO: 1, or its complement, under high stringency conditions, and wherein said polynucleotide encodes an amino acid sequence having the same functional activity as the amino acid sequence of SEQ ID NOs:2 or 4.

* * * * *

SEQUENCE LISTING

```
<160> NUMBER OF SEQ ID NOS: 13

<210> SEQ ID NO 1
<211> LENGTH: 855
<212> TYPE: DNA
<213> ORGANISM: Arabidopsis thaliana
<220> FEATURE:
<221> NAME/KEY: CDS
<222> LOCATION: (63)...(590)

<400> SEQUENCE: 1
tctagaacta gtggatcccc cgggctccag gaattcagca cgaggtttgt tcaagatcaa      60 ag atg tct ata aat ata aga gac cct ctt ata gta agc aga gtt gtt     107
   Met Ser Ile Asn Ile Arg Asp Pro Leu Ile Val Ser Arg Val Val
     1               5                  10                  15 gga gac gtt ctt gat ccg ttt aat aga tca atc act cta aag gtt act     155
Gly Asp Val Leu Asp Pro Phe Asn Arg Ser Ile Thr Leu Lys Val Thr
            20                  25                  30
```

```
tat ggc caa aga gag gtg act aat ggc ttg gat cta agg cct tct cag        203
Tyr Gly Gln Arg Glu Val Thr Asn Gly Leu Asp Leu Arg Pro Ser Gln
             35                  40                  45 gtt caa aac aag cca aga gtt gag att ggt gga gaa gac ctc agg aac        251
Val Gln Asn Lys Pro Arg Val Glu Ile Gly Gly Glu Asp Leu Arg Asn
     50                  55                  60 ttc tat act ttg gtt atg gtg gat cca gat gtt cca agt cct agc aac        299
Phe Tyr Thr Leu Val Met Val Asp Pro Asp Val Pro Ser Pro Ser Asn
 65                  70                  75 cct cac ctc cga gaa tat ctc cat tgg ttg gtg act gat atc cct gct        347
Pro His Leu Arg Glu Tyr Leu His Trp Leu Val Thr Asp Ile Pro Ala
 80                  85                  90                  95 aca act gga aca acc ttt ggc aat gag att gtg tgt tac gaa aat cca        395
Thr Thr Gly Thr Thr Phe Gly Asn Glu Ile Val Cys Tyr Glu Asn Pro
                 100                 105                 110 agt ccc act gca gga att cat cgt gtc gtg ttt ata ttg ttt cga cag        443
Ser Pro Thr Ala Gly Ile His Arg Val Val Phe Ile Leu Phe Arg Gln
             115                 120                 125 ctt ggc agg caa aca gtg tat gca cca ggg tgg cgc cag aac ttc aac        491
Leu Gly Arg Gln Thr Val Tyr Ala Pro Gly Trp Arg Gln Asn Phe Asn
         130                 135                 140 act cgc gag ttt gct gag atc tac aat ctc ggc ctt ccc gtg gcc gca        539
Thr Arg Glu Phe Ala Glu Ile Tyr Asn Leu Gly Leu Pro Val Ala Ala
 145                 150                 155 gtt ttc tac aat tgt cag agg gag agt ggc tgc gga gga aga aga ctt        587
Val Phe Tyr Asn Cys Gln Arg Glu Ser Gly Cys Gly Gly Arg Arg Leu
160                 165                 170                 175 tag atggcttctt cctttataac caatgatatt gcatactctg atgagattta            640
 * tgcatctata gtattttaat ttaataacca ttttatgata cgagtaacga acggtgatga     700
tgcctatagt agttcaatat ataagtgtgt aataaaaatg agaggggag gaaaatgaga     760 gtgttttact tatatagtgt gtgatgcgat aattatatta atctacatga aatgaagtgt    820
tatatttata aaaaaaaaaa aaaaaaaaac tcgag                                855
```

<210> SEQ ID NO 2
<211> LENGTH: 175
<212> TYPE: PRT
<213> ORGANISM: Arabidopsis thaliana

<400> SEQUENCE: 2

```
Met Ser Ile Asn Ile Arg Asp Pro Leu Ile Val Ser Arg Val Val Gly
 1               5                  10                  15

Asp Val Leu Asp Pro Phe Asn Arg Ser Ile Thr Leu Lys Val Thr Tyr
                 20                  25                  30

Gly Gln Arg Glu Val Thr Asn Gly Leu Asp Leu Arg Pro Ser Gln Val
             35                  40                  45

Gln Asn Lys Pro Arg Val Glu Ile Gly Gly Glu Asp Leu Arg Asn Phe
         50                  55                  60

Tyr Thr Leu Val Met Val Asp Pro Asp Val Pro Ser Pro Ser Asn Pro
 65                  70                  75                  80

His Leu Arg Glu Tyr Leu His Trp Leu Val Thr Asp Ile Pro Ala Thr
                 85                  90                  95

Thr Gly Thr Thr Phe Gly Asn Glu Ile Val Cys Tyr Glu Asn Pro Ser
             100                 105                 110

Pro Thr Ala Gly Ile His Arg Val Val Phe Ile Leu Phe Arg Gln Leu
         115                 120                 125
```

```
Gly Arg Gln Thr Val Tyr Ala Pro Gly Trp Arg Gln Asn Phe Asn Thr
    130                 135                 140

Arg Glu Phe Ala Glu Ile Tyr Asn Leu Gly Leu Pro Val Ala Ala Val
145                 150                 155                 160

Phe Tyr Asn Cys Gln Arg Glu Ser Gly Cys Gly Gly Arg Arg Leu
                165                 170                 175

<210> SEQ ID NO 3
<211> LENGTH: 856
<212> TYPE: DNA
<213> ORGANISM: Arabidopsis thaliana

<400> SEQUENCE: 3
ctcgagtttt ttttttttt tttttataa atataacact tcatttcatg tagattaata      60
taattatcgc atcacacact atataagtaa aacactctca ttttcctccc cctctcattt   120
ttattacaca cttatatatt gaactactat aggcatcatc accgttcgtt actcgtatca   180
taaaatggtt attaaattaa aatactatag atgcataaat ctcatcagag tatgcaatat   240
caattggtta taaaggaaga agccatctaa agtcttcttc ctccgcagcc actctccctc   300
tgacaattgt agaaaactgc ggccacggga aggccgagat tgtagatctc agcaaactcg   360
cgagtgttga agttctggcg ccaccctggt gcatacactg tttgcctgcc aagctgtcga   420
aacaatataa acacgacacg atgaattcct gcagtgggac ttggattttc gtaacacaca   480
atctcattgc caaaggttgt tccagttgta gcagggatat cagtcaccaa ccaatggaga   540
tattctcgga ggtgagggtt gctaggactt ggaacatctg gatccaccat aaccaaagta   600
tagaagttcc tgaggtcttc tccaccaatc tcaactcttg gcttgttttg aacctgagaa   660
ggccttagat ccaagccatt agtcacctct ctttggccat aagtaacctt tagagtgatt   720
gatctattaa acggatcaag aacgtctcca caactctgc ttactataag agggtctctt    780
atatttatag acatctttga tcttgaacaa acctcgtgct gaattcctgc agcccggggg   840
atccactagt tctaga                                                    856

<210> SEQ ID NO 4
<211> LENGTH: 110
<212> TYPE: PRT
<213> ORGANISM: Arabidopsis thaliana

<400> SEQUENCE: 4

Met Asp Pro Leu Ile Val Arg Val Gly Asp Val Leu Asp Phe Leu
1               5                   10                  15

Val Tyr Gly Val Thr Asn Gly Leu Pro Ser Gln Val Asn Lys Pro Arg
                20                  25                  30

Val Glu Ile Gly Asp Leu Arg Tyr Thr Leu Val Met Asp Pro Asp Pro
            35                  40                  45

Ser Pro Ser Pro Leu Arg Glu Leu His Trp Leu Val Asp Ile Pro Thr
    50                  55                  60

Thr Phe Gly Glu Ile Val Tyr Glu Pro Pro Gly Ile His Arg Val Phe
65                  70                  75                  80

Leu Phe Arg Gln Arg Gly Arg Asn Phe Asn Thr Arg Phe Ala Tyr Leu
                85                  90                  95

Gly Leu Pro Val Ala Ala Val Phe Asn Gln Arg Glu Arg Arg
            100                 105                 110

<210> SEQ ID NO 5
<211> LENGTH: 112
```

-continued

```
<212> TYPE: PRT
<213> ORGANISM: Arabidopsis thaliana

<400> SEQUENCE: 5

Met Pro Leu Ile Gly Arg Val Gly Asp Val Leu Asp Phe Pro Thr
 1               5                  10                  15

Val Tyr Lys Val Asn Gly Glu Leu Pro Ser Val Lys Pro Arg Val Glu
            20                  25                  30

Ile Gly Asp Leu Arg Thr Leu Val Met Asp Pro Asp Pro Pro Ser Asp
            35                  40                  45

Pro Leu Glu Leu His Trp Val Ile Pro Gly Thr Thr Asp Phe Gly Lys
        50                  55                  60

Glu Val Tyr Glu Pro Arg Pro Gly Ile His Arg Val Phe Val Leu Phe
65                  70                  75                  80

Arg Gln Gln Arg Ser Arg Phe Asn Thr Arg Phe Ala Tyr Asp Leu Gly
                85                  90                  95

Leu Pro Val Ala Ala Val Phe Phe Asn Ala Gln Arg Glu Ala Arg Arg
            100                 105                 110

<210> SEQ ID NO 6
<211> LENGTH: 104
<212> TYPE: PRT
<213> ORGANISM: Arabidopsis thaliana

<400> SEQUENCE: 6

Met Ala Ala Asp Pro Leu Val Gly Arg Val Gly Asp Val Leu Asp Phe
 1               5                  10                  15

Pro Thr Val Gly Lys Thr Asn Gly Glu Pro Ser Asn Pro Val Ile Gly
            20                  25                  30

Thr Leu Val Met Thr Asp Pro Asp Ala Pro Ser Pro Ser Pro Arg Glu
            35                  40                  45

Trp His Trp Val Val Asp Ile Pro Gly Thr Ser Gly Lys Glu Ile Tyr
        50                  55                  60

Pro Arg Pro Pro Gly Ile His Arg Tyr Val Leu Phe Arg Gln Leu Ser
65                  70                  75                  80

Arg Asn Phe Thr Arg Phe Ala Asp Leu Gly Leu Pro Val Ala Val Phe
                85                  90                  95

Asn Ala Gln Glu Ala Arg Arg Arg
            100

<210> SEQ ID NO 7
<211> LENGTH: 69
<212> TYPE: PRT
<213> ORGANISM: Rattus norvegicus

<400> SEQUENCE: 7

Met Ala Ala Pro Leu Val Pro Val Tyr Gly Val Gly Leu Pro Gln
 1               5                  10                  15

Val Asn Pro Gly Asp Leu Tyr Thr Leu Val Thr Asp Pro Asp Ala Pro
            20                  25                  30

Ser Asp Pro Arg Glu Trp His Leu Val Val Gly Asp Ser Gly Tyr Pro
            35                  40                  45

Pro Gly His Arg Tyr Val Gln Gln Leu Gly Arg Phe Phe Tyr Leu Gly
        50                  55                  60

Pro Val Ala Phe Ala
65
```

```
<210> SEQ ID NO 8
<211> LENGTH: 8
<212> TYPE: PRT
<213> ORGANISM: Arabidopsis thaliana

<400> SEQUENCE: 8

Ser Ile Asn Ile Arg Asp Pro Leu
 1               5

<210> SEQ ID NO 9
<211> LENGTH: 11
<212> TYPE: PRT
<213> ORGANISM: Arabidopsis thaliana

<400> SEQUENCE: 9

Glu Asn Met Gly Thr Arg Val Ile Glu Pro Leu
 1               5                  10

<210> SEQ ID NO 10
<211> LENGTH: 9
<212> TYPE: PRT
<213> ORGANISM: Antirrhinum majus

<400> SEQUENCE: 10

Ala Ala Lys Val Ser Ser Asp Pro Leu
 1               5

<210> SEQ ID NO 11
<211> LENGTH: 7
<212> TYPE: PRT
<213> ORGANISM: Arabidopsis thaliana

<400> SEQUENCE: 11

Ala Ala Ser Val Asp Pro Leu
 1               5

<210> SEQ ID NO 12
<211> LENGTH: 11
<212> TYPE: PRT
<213> ORGANISM: Rattus norvegicus

<400> SEQUENCE: 12

Ala Ala Asp Ile Ser Gln Trp Ala Gly Pro Leu
 1               5                  10

<210> SEQ ID NO 13
<211> LENGTH: 11
<212> TYPE: PRT
<213> ORGANISM: Homo sapiens

<400> SEQUENCE: 13

Pro Val Asp Leu Ser Lys Trp Ser Gly Pro Leu
 1               5                  10
```